(12) United States Patent
Cecchi (10) Patent No.: US 9,169,460 B2
(45) Date of Patent: Oct. 27, 2015

(54) FLOODING DISH AND METHOD FOR CHANGING MEDIA IN THE DISH IN THE PREPARATION OF MAMMALIAN SPECIMEN CULTURE AND FOR CRYO-PRESERVATION, FREEZING, VITRIFICATION AND THE THAWING AND WARMING OF SUCH SPECIMENS

(75) Inventor: Michael D. Cecchi, Madison, CT (US)

(73) Assignee: LIFEGLOBAL GROUP LLC, Guilford, CT (US)

( * ) Notice: Subject to any disclaimer, the term of this patent is extended or adjusted under 35 U.S.C. 154(b) by 1642 days.

(21) Appl. No.: 12/454,400

(22) Filed: May 19, 2009

(65) Prior Publication Data

US 2010/0297600 A1    Nov. 25, 2010

(51) Int. Cl.
*C12M 1/00* (2006.01)
*C12M 1/32* (2006.01)
*C12M 3/00* (2006.01)

(52) U.S. Cl.
CPC .............. *C12M 29/00* (2013.01); *C12M 21/06* (2013.01); *C12M 23/12* (2013.01)

(58) Field of Classification Search
CPC ....... C12M 29/00; C12M 21/06; C12M 23/12
See application file for complete search history.

(56) References Cited

U.S. PATENT DOCUMENTS 3,753,357 A    8/1973  Schwartz ........................... 62/64
5,160,312 A *  11/1992 Voelkel ............................ 600/34
5,873,254 A    2/1999  Arav ................................. 62/63
6,395,467 B1   5/2002  Fahy et al. ...................... 435/1.3
6,616,858 B2   9/2003  Fahy et al. ....................... 252/70

OTHER PUBLICATIONS

Abe et al. Biol. of Reprod.,72: 1416-1420,2005.*
Cho et al. Human Reproduction, 17(9):2419-2422,2002.*

* cited by examiner

*Primary Examiner* — Thaian N Ton
(74) *Attorney, Agent, or Firm* — William W. Jones (57) ABSTRACT

A tray assembly which may include a single well or a plurality of wells that will contain specimens for cryo-preservation, freezing, thawing, or warming. The assembly will include a structure whereby a sequence of different media solutions can be introduced into a well or wells in the assembly without the need to move the specimens and without disturbing an overlying oil layer which floats on top of the media solutions. The media solutions will be introduced into the specimen wells through adjunct passages which communicate with the interior of the wells. The adjunct passages will preferably be integral with the wells and will be formed at the same time the wells are formed. Thus manufacturing the assembly of this invention will be inexpensive and repetitive. The adjunct passages can be used to infuse different media solutions into the wells at different stages of the protocols in question. The wells can be inverted cones or pyramids in shape. This shape allows the infusion of sequential media solutions beneath the overlying oil layer, without disturbing the specimen and without significantly elevating the solution level in the wells. The conical or pyramidal shapes also enable the user to readily locate and handle the specimens because the specimens will always gravitate to the nadir of the conical or pyramidal bottom of the wells. This shape also allows the user to see any media level indices placed on the side walls of the wells.

15 Claims, 5 Drawing Sheets

FLOODING DISH AND METHOD FOR CHANGING MEDIA IN THE DISH IN THE PREPARATION OF MAMMALIAN SPECIMEN CULTURE AND FOR CRYO-PRESERVATION, FREEZING, VITRIFICATION AND THE THAWING AND WARMING OF SUCH SPECIMENS

TECHNICAL FIELD

This invention relates to an apparatus and method for the preparation of mammalian cells and tissue specimens for culturing, growing, transferring, cryo-preserving, freezing and vitrifying and the thawing and warming of such specimens, and the use of sequential media products. The method consists of the use of media compositions and multiple stages of preparation. The apparatus is particularly useful for these processes as it reduces the moving of the specimens from one solution on another by the infusion and withdrawal of these fluids within the areas in which the specimens are held and thereby reducing the amount of times the specimens are moved among these solutions thus reducing the risk of damaging the specimens and improving results.

BACKGROUND ART

Biological organisms such as stem cells, tissues, including, but not limited to, immature oocytes, gametes, zygotes, embryos, cleavage stage embryos, blastocyst stage embryos, and the like, are commonly cultured, grown, and may be preserved by freezing and/or vitrification. Petri dishes are generally designed for use by the individual technician for use in a broad range of procedures and applications. Currently there is no Petri dish or similar device that is specifically designed for use during the preparation of the specimens for specimen culture and freezing and/or for thawing the specimens. More specifically, there is no dish or other device that is designed to be used for the multi step preparation of human or animal specimens in the specimen culturing and cryo-preservation and thawing processes.

Currently, there are two methods used for the cryo-preservation of the aforesaid types of specimens, the first of which is referred to as conventional cryo-preservation, and second of which is referred to as vitrification.

The conventional cryo-preservation method refers to the forming of ice crystals during the freezing process and the removal of such ice crystals during the thawing process.

The conventional vitrification method refers to the solidification of the specimens in a solution of reduced and lowered temperature, not by ice crystallization formation, but by extreme elevation of sample viscosity during cooling. Then the specimens are warmed as opposed to thawed. The amounts of specific materials, such as cryo-preservatives and culture medium may vary between the methods.

We will refer herein to these two different methods as being interchangeable, although they may vary in the number of steps, materials and terminologies used when performing certain different procedures or protocols. Therefore, for the purpose of describing procedures, steps or protocols herein, we will refer to "freeze" or "vitrification" when the specimen is being prepared for either of the procedures of cryopreservation, or being prepared for storage, and "thaw" when the specimen is subjected to warming or being taken out of the cryopreservation state.

The problems posed by the current methodology is that technicians are relying on common Petri dishes in these types of specimen procedures in the preparation of human and animal specimens for cryo-preservation and thawing. These dishes are not well suited for these procedures since they may not contain a desired number of wells, are not configured to facilitate these types of processes, and do not allow the technician to readily a fixed set of protocols or procedures each time.

Currently, common Petri dishes used to freeze and thaw the specimens may have flat bottoms, may be with or without molded integral multiple wells, and most will not contain the number of wells needed to complete the desired tasks. For those dishes without wells, the technician may simply create a droplet or a micro-droplet of the solution to be used and then put the specimen into those drops. When the dishes have wells, they may have a single well or up to four wells.

The use of micro-droplets also extends the setup time (which may be up to one hour), the time for performing the steps and procedures, and also may put the specimens at risk, by the possibility of the droplets collapsing thereby exposing the specimens to oil, air, and permanent damage. The specimens must also be handled a number of times which puts the specimens at risk of damage.

Additional problems faced by use of these common Petri dishes is that the procedures in question utilize several different media solutions and the technician must use dishes that may not adapt well to the task, or the technician may try to adapt his or her procedures, steps or protocols, and the timing of the steps, to comply with the restrictions imposed by the dishes used. The result is an ineffective performance of the procedures to be followed and thus poor results. The reduced number of wells may also force the individual technicians to use more than one dish adding to the confusion, creating possible errors, and complicating the performance of the procedures.

In these procedures, the use of multiple vials and different types of medium solutions within these vials, which may contain different concentrations of ingredients or greater of lesser amounts of a particular ingredient, will occur.

An example of the above can be where Vial #1 is a washing solution, and is used in the beginning of preparation of human oocytes. The washing solution is a base media and does not contain any cryo-preservatives; a Vial #2 contains the same base media along with 1,2-propanediol (PrOH), ethylene glycol, glycol, as a cryo-preservative; and a Vial #3 contains the same media as Vial #2 plus a small amount of sucrose.

The solutions used for the cryo-preservation procedures may also contain the ingredients in various levels and may use up to five different vials. An example of this is: Vial #1 may contain 100% base media; Vial #2 may contain 90% media and 10% PrOH; Vial #3 may contain 80% media and 20% PrOH; Vial #4 may contain 70% media and 30% PrOH; and Vial #5 may contain 60% media and 40% PrOH. Thus each of the successive step vials contains a solution in which a specimen is to be immersed, with each of the solutions containing progressively less media and progressively more of the cryo-protectant. The successive specimen treatment steps are timed steps, with the time specimen immersion time for each step being from five to ten minutes, depending on the established protocol in use. Certain protocols in thawing currently use seven different solutions in seven separate vials. These protocols take at least thirty five minutes to complete. The specimens are transferred from one solution to the next during the protocol. Transferring the specimens puts them at risk of damage. Thus, the present protocols which require transferring the specimens from one solution to another are labor intensive, equipment intensive, and present a risk of damage to the specimens during the treatment protocol.

The above-noted protocols for specimen treatment also require that the media and cryo-protectant solutions be overlain in the dish wells with a mineral or paraffin oil to prevent the solutions from evaporating during the treatment steps. The mineral or paraffin oil covers complicate the procedure since the technician must not pick up the oil in the micro tools used to transfer the specimens from one solution to the next. Thus, in order to perform the present protocols, the vials must be placed in the proper order or sequence, to properly prepare the specimens for cryo-preservation or thawing.

Current dishes require the technician to move the specimens from one solution to the next by the use of micro tools and microscopes to find and move the specimens. This is very time and equipment consuming, and the multiple handling of the specimens can also contribute to the problem of growing and survival of the specimens during the protocol in question.

Currently, researchers in stem cell work utilize a series of media solutions, adding ingredients or additional media at specified time intervals and may at times add supplements such as growth hormones and proteins. The cells being grown remain in the desired dish or apparatus for several days, or even for up to two-three weeks. In this procedure, it would be desirable to add additional medium ingredients or additives without having to move the cells, and to be able to change the overall concentrations of certain ingredients by adding ingredients at various times.

It would be desirable to provide an apparatus and method for performing multi-step protocols for preparing specimens for cryo-preservation and/or thawing which does not require multiple vials for containing varying solution concentrations, and which does not require physically transferring specimens being treated in the protocol from one solution vial to another.

It would be highly desirable to provide an apparatus which will promote the growth of stem cells or cells and the changing of the ingredient concentrations without moving the specimens and by adding or withdrawing medium and other components.

DISCLOSURE OF THE INVENTION

This invention relates to a method and apparatus for use in the preparation of specimens for several procedures and methods of treatment, including cryo-preservation or vitrification and/or for thawing or cooling of frozen or vitrified specimens. The method and apparatus are used in the cryo-preservation and thawing of specimens which can include mammalian embryos, oocytes, immature oocytes, ovarian tissue, and which may also be used in connection with additional types of cells, tissues, or stem cells. The apparatus will preferably take the form of a dish which may be made from a polymer, preferably polystyrene, or some other material suitable for use with cells and tissues, and which may be post-molding treated with the chemical Corona to prepare its surface for such uses. The material must be embryo safe and nontoxic, and must be durable enough so as not to scratch easily and be able to maintain its shape. The material should be dear so that its contents may be monitored with a microscope with little or no distortion.

The specimen dish is particularly adapted for the cryo-preservation of human oocytes. Human oocytes are large single cells and thus are difficult to freeze and thaw so that they may be thereafter be fertilized and thereafter result in a live birth. This is due in part to the difficult nature of freezing oocytes in general, but also to the lack of consistency and treatment of the oocytes when being prepared for freezing and thawing.

The dish of this invention will provide consistency of oocyte treatment and will also allow the technicians to be more consistent regarding the liquid medium solutions utilized, and the timing of each step during the procedure by utilizing the control features incorporated into the dish of this invention.

The dish may contain a single well or a plurality of wells that will contain the specimens for cryo-preservation, freezing, thawing, or warming. The dish will include a structure whereby the media solutions can be introduced into the well or wells without the need to transfer the specimens and without disturbing the overlying oil floating on top of the media solutions.

The media solutions will be introduced into the specimen wells through adjunct passages which communicate with the interior of the wells. The adjunct passages will preferably be integral with the dishes and will be formed at the same time the dishes are formed. Thus manufacturing the dishes of this invention will be inexpensive and repetitive. The adjunct passages can be used to infuse different media solutions into the wells at different stages of the protocols in question.

The wells can be conical or pyramidal in shape. This shape allows the infusion of sequential media solutions, as described above, beneath the overlying oil layer, without disturbing the specimen and without significantly elevating the solution level in the wells. The conical shape also enables the user to readily locate and handle the specimens because the specimens always gravitate to the nadir of the conical or pyramidal bottom of the wells.

This shape also allows the user to see any indices on the side wall of the wells.

The conical or pyramidal shape of the wells also allows the technician to cover the media solution with a layer of oil which will thin out stepwise as the volume of the media solution is increased beneath the oil layer. The shape of the wells allows the oil layer to thin out as the well is "filled" with media solution without risking spillage of the oil layer from the wells.

Another significant aspect of the conical or pyramidal shape of the wells is that it allows a much greater flexibility in changing the solution concentrations in the wells due to the large ratios of volumes available to the technician as the volumes available in the wells will increase as the cross sectional area of the dish increases.

It will be appreciated that this invention will allow the user to put an appropriate volume of a first solution of 100% media in one or more of the wells being used. The specimens which are being prepared to be frozen are then placed, one in each of the wells, for culturing in the wells. A layer of oil may then be added to the top of the media solution in each of the wells to limit evaporation of the media from the wells. A syringe is used to add PrOH, isopropanol, glucose, or any desired cryoprotectant, in steps to the media solution. In this example, the syringe is filled with 100% PrOH. The PrOH can be administered to the media solution in the wells in steps as will be disclosed in greater detail herein below. The PrOH can be added to the media either through the oil layer, or through an adjunct passage to the media solution which bypasses the oil layer.

After the specimens have been in the media solution during step 1 of the procedure for the required amount of time, the syringe is used to inject a defined amount of PrOH so as to dilute the media solution to a 90% media/10% PrOH solution during step 2 of the protocol. The specimens are cultured in the step 2 media solution for the prescribed period of time, for example five minutes; and then the syringe is used to further dilute the media solution to an 80% media/20% PrOH solution for step 3 of the protocol. This progressive dilution of the media solution with PrOH from the syringe continues until the protocol in question has been completed.

It will be appreciated that the method and apparatus of this invention enables one to perform a freezing and/or multi step preparation protocol with minimal movement of the specimens being treated, and thus minimal chance of damaging the specimens during performance of the protocol. The protocol dilution levels can be displayed on the side of the wells. The specimens can be protected against media solution evaporation either by an oil layer, or by a physical cover which can be moved into an overlying position relative to the wells during performance of the steps of the protocol in question. The specimens can then be moved from the wells to a freezing straw or a cryo storage device for the final stage of freezing or cryo-preservation of the specimens.

This invention will allow the dilution of various combinations of ingredients to alter the concentrations within the wells. This invention will also be useful to exchange media through the passageways. Media can be withdrawn from the wells through the passageways and through the passages on the sides of the wells. The invention can be used to perform protocols which are used in the sequential use of different media formulations.

In a second example the apparatus is used in the area of human reproduction and IVF. In the area of growth of oocytes, gametes, and embryos, the use of sequential media formulations is commonplace. These media formulations are used in order, in combinations, and separately, for this purpose.

In this example, Media 1 is of a particular formulation of ingredients which will grow or culture the embryo to what is known as the cleavage stage, at about day 2 or 3. At that time, current protocols require the embryo to be moved from Media 1 to Media 2. Media 2 has been placed separately in a Petri dish of prepared micro droplets. The embryo is transferred to the new droplet by pipette. Media 2 contains a variation of Media 1 in which adding, adjusting, or removing ingredients, and the concentrations may vary.

The dish of this invention and the method of use thereof will allow the embryo to remain in a single procedure well in the dish and not have to be moved. This is desirable because moving the embryo can cause damage and shock to the embryo specimens.

The embryos, or other specimens, will remain in Media 1 for the time the protocol requires, then the media will be withdrawn or partially withdrawn and a new Media 2 will be added. The dish and method of this invention may be used in protocols where the media is partially or fully withdrawn from the wells, and then a new media concentration can be added, or the second media can be simply added to the first. The dish and method of this invention can be used for more multiple exchanges or changes of media and combined solutions. The invention also allows for the use of multiple wells which are linked together for multiple specimens.

In this third example, stem cells or somatic cells are deposited into the wells for growth and observation. The cells are then immersed in media for maintenance. The user would then add supplements to the media which may contain such components as protein and growth factors. This will cause the cells to expand. The medium may then be withdrawn from the wells and then a second medium is added. The user then adds a second supplement mixture which includes certain additives such as proteins, and such, which will allow the cells to differentiate into the desired cell types, such as neurons, adipocytes, hepatocytes, or such.

BRIEF DESCRIPTION OF THE DRAWINGS

Objects and advantages of the invention will become more readily apparent from the following detailed description of the invention when taken in conjunction with the accompanying drawings in which.

DETAILED DESCRIPTION OF SPECIFIC EMBODIMENTS OF THE INVENTION

Figure 1:
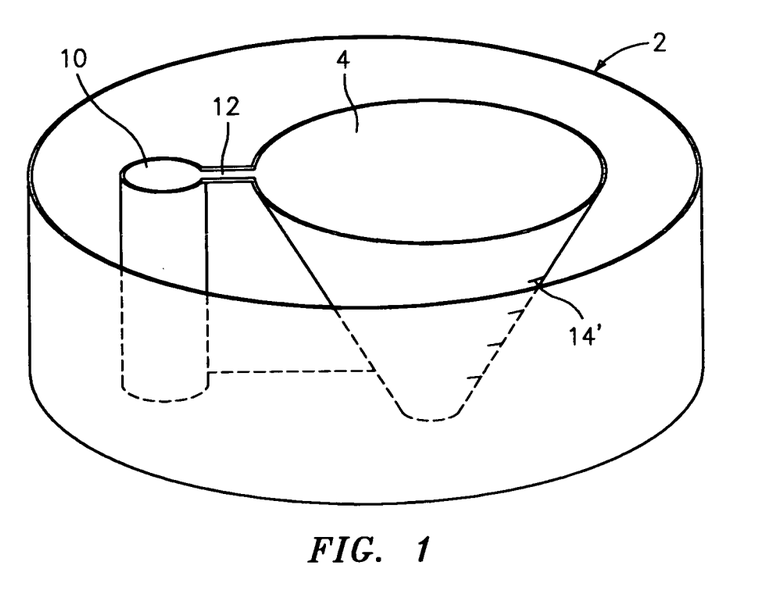
FIG. 1 is a somewhat schematic perspective view of one embodiment of a specimen treatment apparatus which is formed in accordance with this invention.
Figure 2:
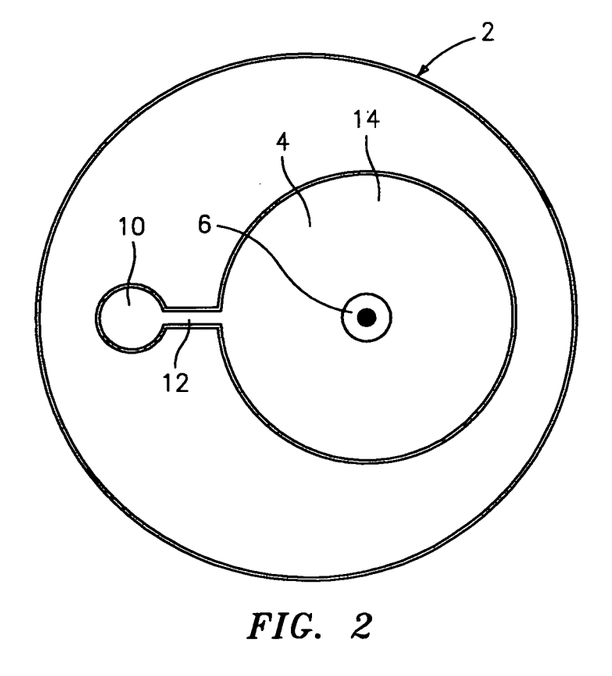
FIG. 2 is a plan view of the apparatus of FIG. 1.

Referring now to the drawings, FIGS. 1 and 2 show a schematic perspective and plan view respectively of a structure for containing specimens which are to be processed in an IVF or other specimen culturing or processing procedure. The structure is denoted generally by the numeral 2 and includes a well 4 having a lowest area 6 into which a specimen placed in the well 4 will migrate. The side wall 14 of the well 4 is tapered inwardly and downwardly so as to ensure that the specimen placed in the well 4 will migrate by gravity to the area 6 in the well 4. The structure 2 includes an adjunct tubular passage 10 which communicates with the well 4 by means of an opening 12. The side wall 14 of the well 4 preferably includes a media level scale 14' whereby the levels of the media mixture solution in the well 4 can be accurately determined.

Figure 3:
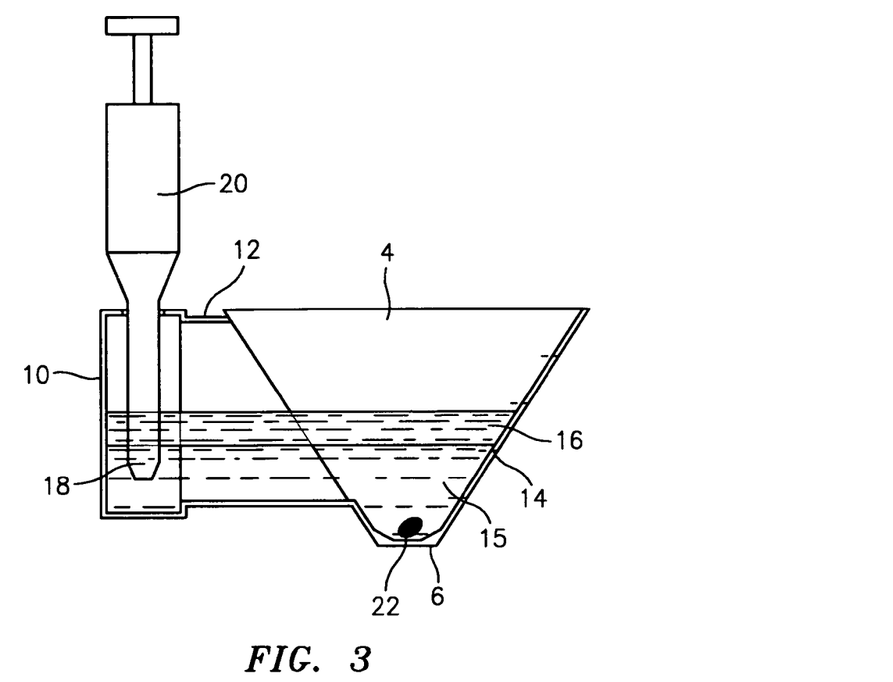
FIG. 3 is a side elevational view showing a syringe component of an assembly which includes the apparatus of FIG. 1.
Figure 4:
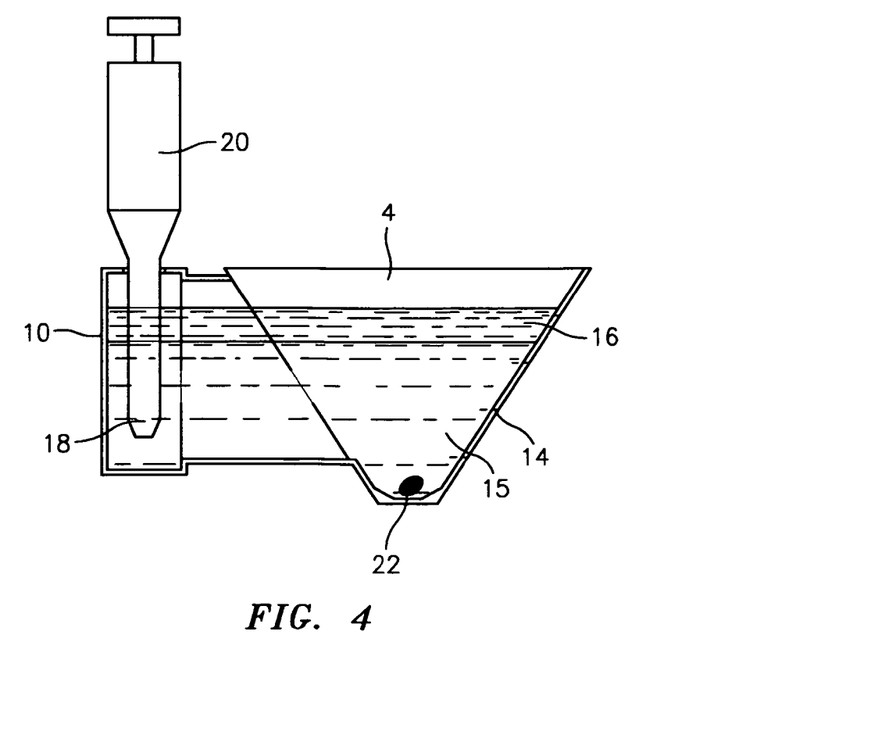
FIG. 4 is a side elevational view similar to FIG. 3 but showing the syringe after it has been used to add a component to a media solution contained in the apparatus.

Referring now to FIGS. 3 and 4, there is shown the use of the structure of FIGS. 1 and 2 to prepare a specimen such as an embryo, ova, stem cell, or the like, for freezing or thawing. The specific procedure described hereinafter will be the preparation of an embryo specimen for freezing. The embryo specimen is denoted by the numeral 22 and is shown where it has descended, in the lowest area 6 in the well 4. FIG. 3 shows the specimen 22 in the well 4 and submerged in a first media composition 15. The media composition 15 can be covered by a layer of oil 16 which prevents evaporation of the media composition 15 from the well 4.

Assuming that the specimen 22 is being prepared for freezing, the first media composition 15 will be a 100% specimen growth media composition. A syringe 20 is positioned in the tubular passage 10 with its lower end 18 extending into the media composition 15. The syringe 20 will be filled with the PrOH component of the composition 15 and the syringe is used to inject a predetermined amount of PrOH into the growth media so as to produce a composition which is 90% growth media and 10% PrOH. After the specimen 22 has remained in the 90/10% composition 15 for the required amount of time, the syringe 20 is actuated to inject a predetermined amount of the PrOH into the composition 15 so as to change the composition 15 to an 80%/20% growth media/ PrOH media composition. The specimen 22 is then allowed to reside in the second composition for the required amount of time, after which the syringe 20 is actuated again to change the composition 15 to a 70%/30% mixture of the growth media and PrOH. This stepwise changing of the composition 15 is continued until a 10% growth media 90%/PrOH composition 15 is reached, as shown in FIG. 4. It will be noted that the tapered configuration of the well 4 allows the addition of the PrOH component into the composition 15 without spilling any of the contents of the well 4, and that the oil layer 16 will simply thin out as the PrOH component is added stepwise to the mixture 15. Thus the mixture 15 is protected against evaporation by the oil layer 16 during the entire procedure. The dilution procedure will preferably continue until a virtual 100% PrOH composition is achieved. This would constitute at least between about a 96% to 98% PrOH composition, or better.

Figure 5:
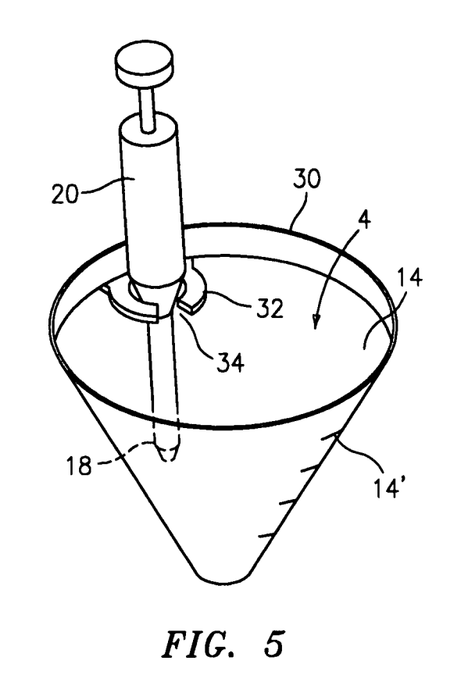
FIG. 5 is perspective view of a second embodiment of an apparatus formed in accordance with this invention.
Figure 6:
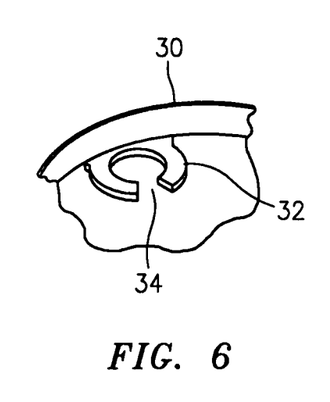
FIG. 6 is a plan view of a segment of the apparatus of FIG. 5.
Figure 7:
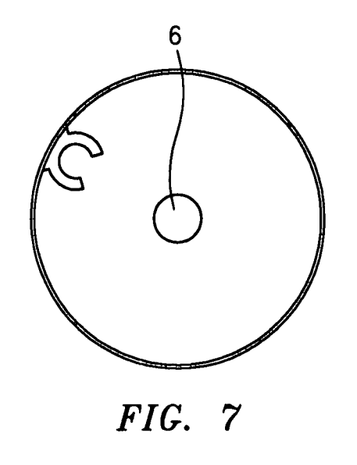
FIG. 7 is perspective view of still another embodiment of an apparatus which has a lid and which is formed in accordance with this invention.

Referring now to FIGS. 5-7 there is shown an alternative embodiment of a structure which can be used to perform the method of this invention described above. The alternative embodiment assembly is denoted generally by the numeral 30. The assembly 30 includes a well 4 having an inwardly and downwardly tapered side wall 14 which may include the media level scale 14' noted above. The well 4 also includes the lowest point area 6 into which a specimen placed in the well 4 will gravitate, as described above. A clip 32 is formed in an upper end of the well 4. The clip 32 serves as a mount for the additive composition syringe 20 described above. The lower end 18 of the syringe 20 will preferably protrude through the oil layer and extend into the initial media solution which contains a specimen placed in the well 4. In procedures which do not require the oil layer, the lower end 18 of the syringe 20 can be disposed above the media and the additive can simply be dropped into the media. The clip 32 may include an opening 34 through which the syringe 20 can be inserted into the clip 32. The alternative embodiment 30 of the assembly can be used in the same manner as the embodiment shown in FIGS. 1-4, which mode of operation is described in detail above.

Figure 8:
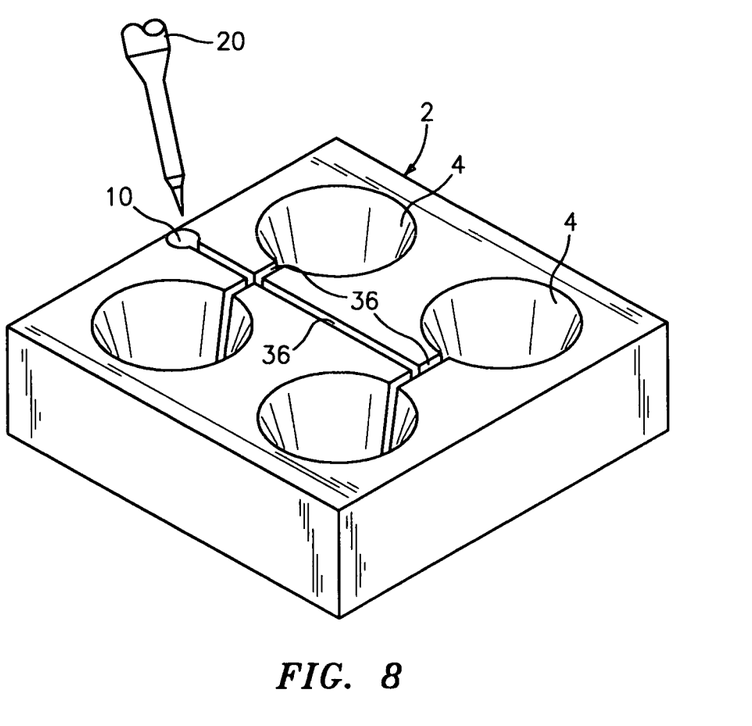
FIG. 8 is a perspective view of still another embodiment of a multi-well variation of a dish formed in accordance with this invention with the wells being interconnected by channels.
Figure 9:
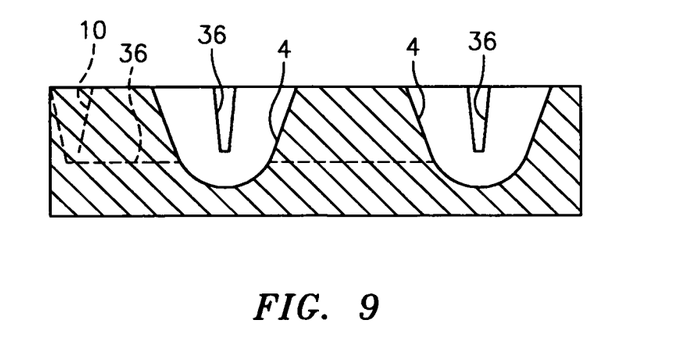
FIG. 9 is a sectional view of the dish of FIG. 8 taken along line 9-9.

FIGS. 8 and 9 show an additional embodiment of the dish 2 wherein the wells 4 are interconnected by passages 36 which connect to the passage 10. The passages 36 allow fluids to be added to or removed from each of the wells 4 by means of the syringe 20.

Figure 10:
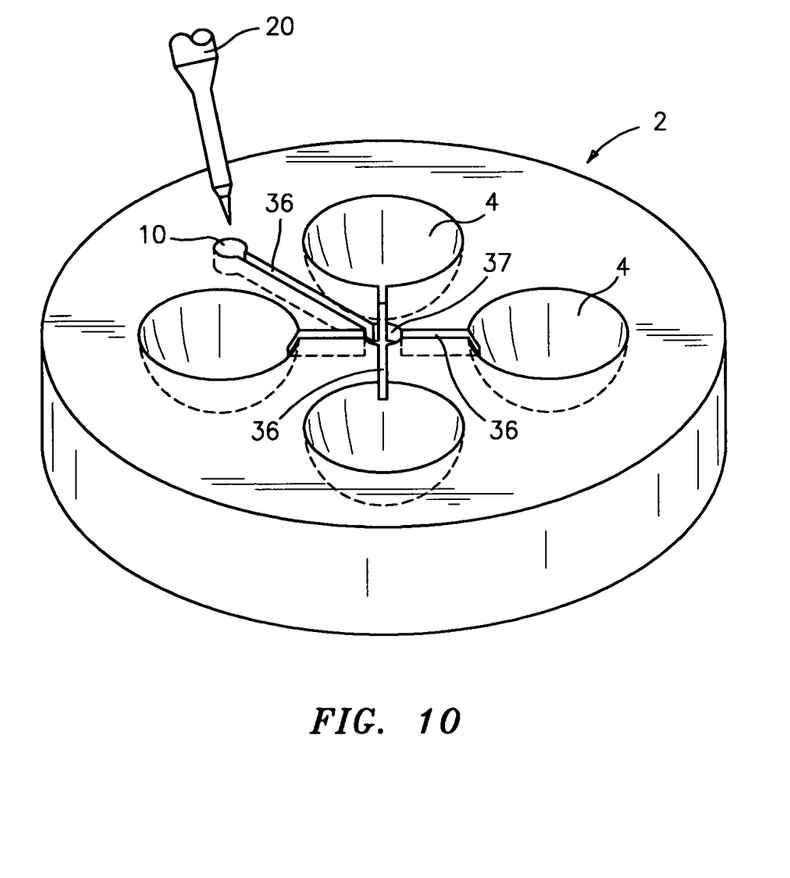
FIG. 10 is a perspective view of still another embodiment of a multi-well variation of a dish formed in accordance with this invention where the wells are interconnected by channels.

FIG. 10 shows an additional embodiment of the dish 2 wherein the wells 4 are interconnected by passages 36 which connect to the passage 10. The passages 36 allow fluids to be added to or removed from each of the wells 4 by means of the syringe 20. In the embodiment shown in FIG. 10, the wells 4 are arranged in a circular fashion arrayed about a central well 37 that connects all of the passages 36 with the passage 10 and the wells 4.

It will be appreciated that the assembly and method of this invention can be used to prepare a wide variety of biological specimens for freezing, thawing and other procedures, such as the altering of an embryo cell culture media composition in order to transform a first overall culture media composition into a second overall culture media composition during an embryo cell culturing protocol, stem cell growth, embryo culture, issue culture, and the like. During the procedures, the specimens will not have to be moved from one site to another during the multiple steps of the procedures, and instead, can remain in one place during the procedures, thus minimizing handling and possible damage to the specimens.

While the invention has been described with respect to preferred embodiments, those skilled in the art will readily appreciate that various changes and/or modifications can be made to the invention without departing from the spirit or scope of the invention as defined by the appended claims.

What is claimed is:

1. A method for performing a culturing and growing procedure on a biological specimen which specimen is suitable for use in research and IVF, said method comprising:
    a) the step of providing said biological specimen in a receptacle containing a predetermined amount of a first liquid and holding said biological specimen in said first liquid for a first predetermined amount of time;
    b) the step of adding a first predetermined amount of a second liquid to said receptacle so as to form a first diluted mixture of said first and second liquids, and holding said biological specimen in said first mixture for a second predetermined amount of time;
    c) the step of adding a second predetermined amount of said second liquid to said receptacle so as to form a second diluted mixture of said first and second liquids, and holding said biological specimen in said second mixture for a second predetermined amount of time; and
    d) repeating steps b) and c) until a diluted mixture of said first and second liquids which is greater than about 50% of said second liquid results.

2. The method of claim 1 comprising the further step of covering said liquids in the receptacle with a layer of oil so as to prevent evaporation of said liquids from the receptacle.

3. The method of claim 1 wherein the dilution of said first liquid with said second liquid is accomplished by adding 10% increments of said second liquid to said first liquid stepwise until the composition of said mixture in the receptacle is greater than about 90% of said second liquid.

4. The method of claim 1 wherein said IVF procedure is the preparation of an embryo, oocyte, stem cell, ovarian tissue, or other specimen for freezing.

5. The method of claim 4 wherein said first liquid is a culturing media for said specimen.

6. The method of claim 5 wherein said second liquid is antifreeze or a cryoprotectorant.

7. The method of claim 6 wherein said second liquid is PrOH, ethylene glycol, glycol, or sucrose.

8. The method of claim 1 wherein said procedure is a thawing or recovery procedure for specimens after cryofreezing or vitrification.

9. The method of claim 1 wherein said procedure involves reviving specimens from a cryo state by diluting of cryoprotectorants in a series of cryoprotectorant dilution steps.

10. A method for preparing an embryo specimen, oocyte specimen, stem cell specimen, ovarian tissue specimen, or other biological specimen for vitrification or freezing, said method comprising:
    a) the step of placing said specimen in a receptacle containing a first liquid mixture of a specimen culturing medium and a cryoprotectorant wherein the amount of culturing medium in said first mixture exceeds the amount of cryoprotectorant in said first mixture in said receptacle;

b) the step of holding said specimen in said first mixture for a predetermined amount of time in said receptacle;

c) the step of diluting said first mixture by adding a predetermined amount of said cryoprotectorant so as to form a diluted mixture of the specimen culturing medium and the cryoprotectorant wherein the amount of cryoprotectorant is increased in said receptacle;

d) the step of holding said specimen in the diluted mixture for a predetermined amount of time in said receptacle; and e) repeating steps c) and d) until the amount of cryoprotectorant exceeds the amount of culturing medium in the diluted mixture in said receptacle.

11. The method of claim 10 comprising the further step of covering the liquid mixture in the receptacle with a layer of oil so as to prevent evaporation of liquids from the receptacle.

12. The method of claim 10 wherein the dilution of the diluted liquid mixtures with said cryoprotectorant is accomplished by adding 10% increments of said cryoprotectorant to the diluted mixtures stepwise until the composition of the diluted mixture in the receptacle is greater than about 90% of said cryoprotectorant.

13. A method for thawing or devitrifying a frozen or vitrified embryo specimen, oocyte specimen, stem cell specimen, ovarian tissue specimen, or other biological specimen for culturing, said method comprising:

a) the step of placing said specimen in a receptacle containing a first liquid mixture of a specimen culturing medium and a cryoprotectorant wherein the amount of cryoprotectorant in said first mixture exceeds the amount of culturing medium in said first mixture;

b) the step of holding said specimen in said first mixture for a predetermined amount of time in said receptacle;

c) the step of diluting said first mixture by adding a predetermined amount of said culturing medium so as to form a diluted mixture of the specimen culturing medium and the cryoprotectorant wherein the amount of culturing medium is increased in said receptacle;

d) the step of holding said specimen in said diluted mixture for a predetermined amount of time in said receptacle; and e) repeating steps c) and d) until the amount of culturing medium exceeds the amount of cryoprotectorant in the diluted mixture in said receptacle.

14. The method of claim 13 comprising the further step of covering said liquids in the receptacle with a layer of oil so as to prevent evaporation of said liquids from the receptacle.

15. The method of claim 13 wherein the dilution of the diluted liquid mixtures with said culturing medium is accomplished by adding 10% increments of said culturing medium to the diluted mixtures stepwise until the composition of the diluted mixture in the receptacle is greater than about 90% of said culturing medium.

* * * * *